United States Patent [19]

Felföldi et al.

[11] 4,250,310

[45] Feb. 10, 1981

[54] 3-[4-(3-METHOXY-PHENYL)-PIPERAZIN-1-YL]-1-(FURAN-2-CARBONYLOXY)-PROPANE

[75] Inventors: Karoly Felföldi; József Apjók; Mihaly Bartok; József Czombos; Arpád Molnár; Ferenc Noteisz, all of Szeged; Egon Karpati; László Szporny, both of Budapest, all of Hungary

[73] Assignee: Richter Gedeon Vegyeszeti Gyar R.T., Budapest, Hungary

[21] Appl. No.: 974,082

[22] Filed: Dec. 28, 1978

Related U.S. Application Data

[62] Division of Ser. No. 859,928, Dec. 12, 1977, Pat. No. 4,140,790.

[30] Foreign Application Priority Data

Dec. 15, 1976 [HU] Hungary .............................. RI 605

[51] Int. Cl.³ ............................................ C07D 405/12
[52] U.S. Cl. ...................................... 544/379; 424/250
[58] Field of Search ............... 424/250; 544/392, 379, 544/399, 359, 394

[56] References Cited

U.S. PATENT DOCUMENTS

| | | | |
|---|---|---|---|
| 3,929,792 | 12/1975 | Bouchara | 544/394 |
| 3,953,449 | 4/1976 | Giudicelli et al. | 544/394 |
| 4,140,790 | 2/1979 | Felfoldi et al. | 544/375 |

Primary Examiner—Jose Tovar
Attorney, Agent, or Firm—Karl F. Ross

[57] ABSTRACT

Piperazine derivatives having the formula (I)

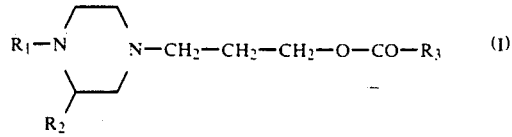

wherein
$R_1$ is $C_{1-5}$ alkyl group which can have a phenyl, trimethoxyphenyl, phenoxy, methoxy-cyclohexyl or heptamethyleneimino substituent on the terminal carbon atom, allyl, phenyl which can have one or more halogen, $C_{1-4}$ alkyl, $C_{1-4}$ alkoxy, trihalomethyl or allyl substituents, or $C_{2-5}$ alkoxycarbonyl;
$R_2$ is hydrogen or $C_{1-4}$ alkyl; and
$R_3$ is furyl or a $C_{5-6}$ cycloalkyl having a $C_{1-4}$ alkoxy substituent, and acid addition salts or quaternary salts thereof with anti-arrhythmic and coronary dilatating pharmaceutical effects.

1 Claim, No Drawings

# 3-[4-(3-METHOXY-PHENYL)-PIPERAZIN-1-YL]-1-(FURAN-2-CARBONYLOXY)-PROPANE

CROSS-REFERENCE TO RELATED APPLICATION

This application is a division of Ser. No. 859,928 filed Dec. 12, 1977, now U.S. Pat. No. 4,140,790.

DESCRIPTION OF THE INVENTION

This invention relates to piperazine derivatives having the formula (I)

$$R_1-N\diagup\diagdown N-CH_2-CH_2-CH_2-O-CO-R_3 \quad (I)$$
$$\diagdown\diagup$$
$$R_2$$

wherein
$R_1$ is $C_{1-5}$ alkyl group which can have a phenyl, trimethoxyphenyl, phenoxy, methoxy-cyclohexyl or heptamethyleneimino substituent on the terminal carbon atom, allyl, phenyl which can have one or more halogen, $C_{1-4}$ alkyl, $C_{1-4}$ alkoxy, trihalomethyl or allyl substituent, or $C_{2-5}$ alkoxycarbonyl;
$R_2$ is hydrogen or a $C_{1-4}$ alkyl; and
$R_3$ is furyl or $C_{5-6}$ cycloalkyl having a $C_{1-4}$ alkoxy substituent, and pharmaceutically effective acid addition salts or quaternary salts thereof.

The invention also relates to a process for the preparation of the above compounds.

Esters of 3-(4-substituted)-piperazino-1-yl-1-hydroxy-propane formed with di- and trimethoxybenzoic acid have already been described in the literature. The known compounds belonging to this group possess tranquillizing effects (Chem. Abstr. 53, 16,170 b), act on the central nervous system [Bull, Soc. Chim. France 576–580 (1959)], improve the oxygen supply of the coronary artery (British Pat. No. 1,127,993) or have sedative and tranquillizing effects (U.S. Pat. No. 3,038,901).

The novel compounds of the formula (I) are esters of 3-[(4-substituted)-piperazino-1-yl]-1-hydroxy-propanes formed with furan-2-carboxylic acid, xanthene-9-carboxylic acid or alkoxy-cycloalkylcarboxylic acids, and have anti-arrhythmic and coronary dilating effects.

The novel compounds of the formula (I), wherein $R_1$, $R_2$, and $R_3$ are as defined above, are prepared according to the invention by reacting a compound of the formula (II), $$R_1-N\diagup\diagdown N-CH_2-CH_2-CH_2-OH \quad (II)$$
$$\diagdown\diagup$$
$$R_2$$

with a carboxylic acid of the formula (III), $$R_3-COOH \quad (III)$$

or a reactive derivative thereof. If desired, the resulting compounds can be converted into their pharmaceutically effective acid addition salts or quaternary ammonium salts.

The carboxylic acids of the formula (III) and their reactive derivatives are commonly known substances. Preferred methods for the preparation of the starting substances having the formula (II) are described in Examples 1a and 2a.

According to one of the method aspects of the invention, free acids of the formula (III) are used as acylating agents. In such instances the compounds of the formulae (II) and (III) are reacted with each other preferably in the presence of a carboxy activator and/or a dehydrating agent. As carboxy activators, the halophenols and nitro-halophenols, such as pentachlorophenol, have to be particularly effective. A further preferred activator is N,N'-dicyclohexyl-carbodiimide, which can be used optionally in combination with a phenol-type activator.

According to a preferred method of the invention a reactive derivative of an acid of the formula (III) is used as an acylating agent. The reactive carboxylic acid derivatives can be the appropriate anhydrides, halides and esters formed with $C_{1-5}$ aliphatic alcohols.

If an acid halide, preferably an acid chloride, is used as acylating agent, the acylating agent is reacted with the compound of the formula (II) in a molar ratio of 1:1.0 to 1:1.1.

The reaction can be performed in the presence of a dry inert organic solvent, such as benzene or a homolog thereof (e.g. toluene or xylene), a chlorinated hydrocarbon (e.g. chloroform, carbon tetrachloride) or an aliphatic ketone (e.g. acetone or methyl-isobutyl-ketone).

The reaction temperature may vary within wide limits; it is preferred, however, to introduce the acylating agent into the mixture under cooling (at a temperature of preferably 0° to 30° C.) and then to heat the mixture to an elevated temperature, preferably to the boiling point. The acid addition salt of the end product can be separated directly from the reaction mixture and it can be isolated e.g. by filtration.

If a $C_{1-5}$ aliphatic ester of an acid having the formula (III) is used as the acylating agent, the reaction is performed preferably in the presence of a catalytic amount of an alkali alcoholate, particularly sodium or potassium methylate or ethylate. The acylating agent is applied in 2 to 3 molar excess.

The reaction is performed either in the presence of a solvent listed above or in the absence of solvents.

The reaction temperature may vary within wide limits, generally between 35° C. and 150° C. According to a preferred method the reaction is performed at the boiling point of the mixture; in such instances the $C_{1-5}$ alcohol splitting off during the reaction can be removed from the system by distillation. The resulting product can be isolated from the cooled reaction mixture by extraction or related methods.

The free bases of the formula (I) can be separated and purified according to known methods; they can be converted, however, into their acid addition salts or quaternary salts without separation and purification.

The acid addition salts are prepared by reacting the free base with an organic or mineral acid, such as a hydrohalide (e.g. hydrochloric, hydrobromic or hydroiodic acid), sulfuric acid, phosphoric acid, acetic acid, propionic acid, butyric acid, maleic acid, fumaric acid, citric acid, malic acid, tartaric acid, etc.

Quaternary salts are formed advantageously by reacting the free bases with $C_{1-5}$ alkyl halides, other quaternarizing agents are, however, equally applicable. The only requirement in this connection is that the anion of the quaternary salt should be physiologically tolerable and pharmacologically acceptable.

The quaternary salts are prepared by methods known per se, e.g. by dissolving the free base of the formula (I) in an organic solvent, preferably in an aliphatic ketone, and introducing the quaternarizing agent into the solution. The reaction mixture is gently heated, then cooled, and the separated quaternary salt is filtered off.

The progress of the reactions can be monitored preferably by thin layer chromatography, applying e.g. silica gel HF (activated at 100° C.) as adsorbent, a 95:5 mixture of ethanol and aqueous ammonia as solvent and Draggendorf reagent or iodine vapor as a developing agent.

As has been mentioned above, the compounds of the formula (I) exert anti-arrhythmic and coronary dilatating effects.

The coronary dilating effects of the compounds were examined on an isolated rat heart according to the method of Langendorff [E. Vanremoortere et al.: Arch. Int. Pharmacodyn. 95, 466 (1953)]. Six tests were performed with each of the compounds for each of the dosages examined. The results indicated in Table 1 are the averages of the results observed in the individual tests. The coronary flow, characteristic of the extent of artery dilatation, was measured prior to and after administering the compound in question, and the increase induced by the compound was expressed in percentages in relation to the initial value. As a reference substance dipyridamol, a compound applied successfully in therapy, was used.

The anti-arrhythmic effects of the compounds were examined on narcotized cats [L. Szekeres, J. Papp: British J. Pharmacol. 17, 167 (1967)]. The electric fibrillation threshold value of the heart was determined prior to and after administering the drug, and the increase provoked by the compound administered was expressed in percentages in relation to the initial value. Six tests were performed with each of the compounds for each of the dosages examined. The results indicated in Table 1 are the averages of the results obtained in the individual tests. As reference substance chinidine, a compound applied successfully in the therapy as anti-arrhythmic agent, was used.

The compound numbers given in Table 1 represent the following compounds:

1878: 3-(4-ethoxycarbonyl-piperazin-1-yl)-1-(xanthene-9-carbonyloxy)-propane hydrochloride
1879: 3-[4-(3-heptamethyleneimino-propyl)-piperazin-1-yl]-1-(xanthene-9-carbonyloxy)-propane trihydrochloride
1880: 3-[4-(2-phenoxy-ethyl)-piperazin-1-yl]-1-(xanthene-9-carbonyloxy)-propane dihydrochloride
1909: 3-[4-(3-methoxy-phenyl)-piperazin-1-yl]-1-(furan-2-carbonyloxy)-propane dihydrochloride
1977: 3-(4-allyl-piperazin-1-yl)-1-(xanthene-9-carbonyloxy)-propane dihydrochloride
1981: 3-(4-benzyl-piperazin-1-yl)-(xanthene-9-carbonyloxy)-propane dihydrochloride
1986: 3-(4-butyl-piperazin-1-yl)-1-(xanthene-9-carbonyloxy)-propane dimethoiodide

TABLE 1

| Compound No. | Increase of fibrillation threshold, % | | | Increase of coronary flow, % | |
|---|---|---|---|---|---|
| | 2.0 mg/kg | 1.0 mg/kg | 0.5 mg/kg | 0.5 /μg/heart | /μg/heart |
| 1878 | | 21.5 | 13.2 | 31.6 | 13.5 |
| 1879 | | | | 28.3 | 22.1 |
| 1880 | | 22.4 | | | |
| 1909 | | 30.3 | 14.2 | | |
| 1977 | | 27.6 | 18.9 | | |
| 1981 | | | | 27.7 | 21.4 |
| 1986 | 31.1 | | | | |
| Chinidine | 34.5 | 20.6 | | | |
| Dipyridamol | | | | 27.7 | 17.8 |

The data of Table 1 clearly indicate that the effects of the compounds tested are superior to those of the reference substances.

The compounds with coronary dilatating effects are used in human therapy as intravenously administerable compositions for the treatment of acute attacks or as orally or rectally administerable compositions for the treatment of chronic disorders. Depending on the status of the patient, the compounds can be administered in single dosages of 0.05 to 0.6 mg/kg, whereas the total daily dosage can vary within 0.2 and 1.5 mg/kg, preferably 0.6 to 1.5 mg/kg.

The compounds with anti-arrhythmic effects can be used in human therapy primarily as compositions administerable by oral or intravenous route. Depending on the severity of the disorder, the compounds can be administered in single oral or intravenous dosages of 1.0 to 3.0 mg/kg body weight, whereas the total daily dosage can vary within about 1 to 10 mg/kg body weight, preferably about 3 to 7 mg/kg body weight.

The compounds according to the invention may be converted into pharmaceutical compositions by admixing them with inert, non-toxic, solid or liquid carriers and/or auxiliary agents generally used in the pharmaceutical industry. As carriers, e.g. water, gelatin, lactose, starch, talc, magnesium stearate, vaseline, gum arabic, vegetable oils, polyethylene glycols, etc., can be used. The pharmaceutical compositions may contain optionally various auxiliary agents, such as preserving agents, stabilizing agents, wetting agents, emulsifying agents, buffers, flavoring agents, etc.

EXAMPLE 1

3-[4-(2-Methoxyphenyl)-piperazin-1-yl]-1-(xanthene-9-carbonyloxy)-propane hydrochloride (A)

3-[4-(2-Methoxyphenyl)-piperazin-1-yl]-1-hydroxy-propane 46 g of 1-(2-methoxyphenyl)-piperazine and 24.5 g of trimethylene chlorohydrine are dissolved in 200 ml of ethanol, and 25 g of potassium carbonate are added to the solution. The mixture is refluxed for 30 hours, thereafter it is cooled to 0° C., diluted with 50 ml of ethyl ether, filtered, and the filtrate is evaporated. The residue is dissolved in 100 ml of 50° C. benzene, the solution is cooled to 0° C., and allowed to stand for 10 hours. The separated crystals are filtered off and dried. 46 g (77%) of 3-[4-(2-methoxyphenyl)-piperazin-1-yl]-1-hydroxy-propane are obtained; m.p.: 92°–93° C.

By the proper selection of the starting substances the following compounds can be prepared in the manner described above:

3-(4-phenyl-piperazin-1-yl)-1-hydroxy-propane; m.p.: 73°–74° C.;

3-(4-ethoxycarbonyl-piperazin-1-yl)-1-hydroxy-propane; b.p.: 150° C./2 mm Hg, $n_D^{25}$: 1.4820;

3-[4-(3-trifluoromethylphenyl)-piperazin-1-yl]-1-hydroxy-propane; b.p.: 158°–160° C./2 mm Hg;

3-[4-(3-methoxyphenyl)-piperazin-1-yl]-1-hydroxy-propane; m.p.: 94°–95° C.;

3-[4-4-methoxyphenyl)-piperazin-1-yl]-1-hydroxy-propane; m.p.: 87°–89° C.;

3-[4-(4-methylphenyl)-2-methyl-piperazin-1-yl]-1-hydroxypropane; m.p.: 69°–71° C.;

3-[4-(2,5-dimethylphenyl)-piperazin-1-yl]-1-hydroxy-propane; m.p.: 65°–67° C.;

3-[4-(3,4,5-trimethoxybenzyl)-piperazin-1-yl]-1-hydroxy-propane; m.p.: 85°–87° C.;

3-[4-(3-methoxy-cyclohexylmethyl)-piperazin-1-yl]-1-hydroxy-propane; $n_D^{20}$: 1.5570;

3-[4-(3-phenylpropyl)-piperazin-1-yl]-1-hydroxy-propane; $n_D^{20}$: 1.5326;

3-[4-(3-heptamethyleneiminopropyl)-piperazin-1-yl]-1-hydroxy-propane; m.p.: 93°–94° C.;

3-[4-(2-phenoxyethyl)-piperazin-1-yl]-1-hydroxy-propane hydrochloride; m.p.: 132°–134° C.;

3-[4-(2-{2-methoxyphenyl}-ethyl)-piperazin-1-yl]-1-hydroxy-propane; b.p.: 172°–175° C./2 mm Hg.

B

3-[4-(2-Methoxyphenyl)-piperazin-1-yl]-1-(xanthene-9-carbonyloxy)-propane hydrochloride A solution of 3.8 g of 3-[4-(2-methoxyphenyl)-piperazin-1-yl]-1-hydroxy-propane in 40 ml of acetone is added dropwise at 20° C. to a stirred solution of 4.9 g of xanthene-9-carbonyl chloride in 30 ml of acetone. The reaction mixture is refluxed for 30 minutes, allowed to cool to 60° C., and then ethanolic hydrochloric acid is added to the mixture until no more crystalline substance separates. The reaction mixture is cooled to 0° C., the separated crude substance is filtered off, and the crude substance is recrystallized from 20 ml of a 1:2 mixture of water and ethanol. 5.3 g (73%) of 3-[4-(2-methoxyphenyl)-piperazin-1-yl]-1-(xanthene-9-carbonyloxy)-propane hydrochloride are obtained; m.p.: 193°–195° C.

Similarly the following compounds are prepared from the appropriate starting substances:

3-(4-ethoxycarbonyl-piperazin-1-yl)-1-(xanthene-9-carbonyloxy)-propane hydrochloride; m.p.: 144°–145° C.;

3-(4-phenyl-piperazin-1-yl)-1-(xanthene-9-carbonyloxy)-propane dihydrochloride; m.p.: 153°–154° C.;

3-[4-(3-trifluoromethylphenyl)-piperazin-1-yl]-1-(xanthene-9-carbonyloxy)-propane dihydrochloride; m.p.: 125°–126° C.;

3-[4-(2-methoxyphenyl)-piperazin-1-yl]-1-(furan-2-carbonyloxy)-propane dihydrochloride; m.p.: 165°–166° C.;

3-[4-(3-methoxyphenyl)-piperazin-1-yl]-1-(furan-2-carbonyloxy)-propane dihydrochloride; m.p.: 180°–181° C.;

3-[4-(3-methoxyphenyl)-piperazin-1-yl]-1-(3-methoxycyclohexyl-carbonyloxy)-propane dihydrochloride; m.p.: 178°–179° C.;

3-[4-(4-methoxyphenyl)-piperazin-1-yl]-1-(furan-2-carbonyloxy)-propane dihydrochloride; m.p.: 162°–163° C.;

3-[4-(4-methylphenyl)-2-methyl-piperazin-1-yl]-1-(xanthene-9-carbonyloxy)-propane dihydrochloride; m.p.: 169°–170° C.;

3-[4-(2,5-dimethylphenyl)-piperazin-1-yl]-1-(xanthene-9-carbonyloxy)-propane dihydrochloride; m.p.: 221°–223° C.;

3-(4-benzyl-piperazin-1-yl)-1-(xanthene-9-carbonyloxy)-propane dihydrochloride; m.p.: 204°–206° C.;

3-[4-(3,4,5-trimethoxybenzyl)-piperazin-1-yl]-1-(xanthene-9-carbonyloxy)-propane dihydrochloride; m.p.: 196°–198° C.;

3-[4-(3-heptamethyleneiminopropyl)-piperazin-1-yl]-1-(xanthene-9-carbonyloxy)-propane trihydrochloride; m.p.: 205°–206° C.;

3-[4-(3-phenylpropyl)-piperazin-1-yl]-1-(xanthene-9-carbonyloxy)-propane dihydrochloride; m.p.: 176°–178° C.;

3-[4-(2-phenoxyethyl)-piperazin-1-yl]-1-(xanthene-9-carbonyloxy)-propane dihydrochloride; m.p.: 182°–183° C.;

3-[4-(3-methoxy-cyclohexylmethyl)-piperazin-1-(xanthene-9-carbonyloxy)-propane dihydrochloride; m.p.: 186°–187° C.

EXAMPLE 2

3-(4-Allyl-piperazin-1-yl)-1-(xanthene-9-carbonyloxy)-propane dihydrochloride (A) 3-(4-Allyl-piperazin-1-yl)-1-hydroxy-propane 32 g of 1-carbethoxy-piperazine and 24.5 g of allyl bromide are dissolved in 70 ml of ethanol. 25 g of calcined potassium carbonate are added to the solution, and the mixture is stirred under reflux for 30 hours. The reaction mixture is cooled to 0° C., the solids are filtered off, and the filtrate is evaporated under reduced pressure. The residue is admixed with 55 ml of concentrated hydrochloric acid, the mixture is boiled for 24 hours and then it is evaporated. The residue is triturated with 30 ml of ethanol and the solid is filtered off. The obtained 27 g of solid 1-allyl-piperazine dihydrochloride are dissolved in 80 ml of water, the aqueous solution is rendered alkaline (pH=8) with 20% aqueous sodium hydroxide solution, and the alkaline mixture is extracted with 3×80 ml of ethyl ether. The etheral extracts are combined, dried over sodium sulfate, filtered, and the ether is evaporated. The resulting 15.5 g of 1-allyl-piperazine are dissolved in 100 ml of ethanol, 12.3 g of trimethylene chlorohydrine and 18 g of calcined potassium carbonate are added to the solution, and the mixture is stirred and refluxed for 30 hours. The reaction mixture is cooled to 0° C., the solids are filtered off, and the filtrate is evaporated. The obtained residue is purified by distillation. In this way 15 g (45%) of 3-(4-allyl-piperazin-1-yl)-1-hydroxy-propane are obtained; b.p.: 98°–100° C./8 mm Hg; $n_D^{20}$: 1.4935.

Similarly the following compounds are prepared from the appropriate starting substances:

3-(4-butyl-piperazin-1-yl)-1-hydroxy-propane; $n_D^{18}$: 1.4775;

3-[4-(3-phenylallyl)-piperazin-1-yl]-hydroxy-propane; b.p.: 165°–168° C./2 mm Hg; $n_D^{25}$: 1.5520.

(B)

3-(4-Allyl-piperazin-1-yl)-1-(xanthene-9-carbonyloxy)-propane dihydrochloride 3-(4-Allyl-piperazin-1-yl)-hydroxy-propane, prepared as described in Example 2, Step A, is reacted with xanthene-9-carbonyl chloride as described in Example 1, Step B. 3-(4-Allyl-piperazin-1-yl)-1-(xanthene-9-carbonyloxy)-propane dihydrochloride is obtained with a yield of 76%; m.p.: 209°–211° C.

Similarly the following compounds are prepared from the appropriate starting substances:

3-(4-butyl-piperazin-1-yl)-1-(xanthene-9-carbonyloxy)-propane dihydrochloride; m.p.: 188°–190° C.;

3-[4-(3-phenylallyl)-piperazin-1-yl]-1-(3-methoxy-cyclohexylcarbonyloxy)-propane dihydrochloride; m.p.: 179°–180° C.;

3-[4-(3-phenylallyl)-piperazin-1-yl]-1-(xanthene-9-carbonyloxy)-propane dihydrochloride; m.p.: 190°–192° C.

EXAMPLE 3

3-(4-Butyl-piperazin-1-yl)-1-(xanthene-9-carbonyloxy)-propane dimethoiodide 5 g of 3-(4-butyl-piperazin-1-yl)-1-(xanthene-9-carbonyloxy)-propane dihydrochloride, prepared as described in Example 2, are admixed with 20 ml of a 5% aqueous solution of sodium hydroxide, and the alkaline solution is extracted with 3×20 ml of ethyl ether. The etheral extracts are combined, dried over sodium sulfate, filtered, and the filtrate is evaporated. The residue is dissolved in 25 ml of acetone, and 3.5 g of methyl iodide are added to the solution. The reaction mixture is refluxed for 15 minutes and then cooled to 0° C. The crystalline product is filtered off and recrystallized from 30 ml of ethanol. 3.5 g of the named compound are obtained; m.p.: 188°–190° C.

Similarly the following quaternary salts are prepared from the appropriate starting substances:

3-(4-phenyl-piperazin-1-yl)-1-(xanthene-9-carbonyloxy)-propane methoiodide, 3-(4-ethoxycarbonyl-piperazin-1-yl)-1-(xanthene-9-carbonyloxy)-propane methoiodide; m.p.: 200° C. (decomposition).

EXAMPLE 4

3-[4-(3-trifluoromethylphenyl)-piperazin-1-yl]-1-(furan-2-carbonyloxy)-propane dihydrochloride 0.5 ml of 10% sodium methoxide solution are added to a mixture of 5.9 g of 3-[4-(3-trifluoromethylphenyl)-piperazin-1-yl]-1-hydroxy-propane and 2.6 g of furan-2-carboxylic acid methyl ester at 60° C., and the reaction mixture is maintained at 100° C. for 2 hours. During this period methanol, forming as a by-product in the reaction, distills off. The reaction mixture is admixed with 50 ml of benzene and the resulting solution is extracted with 10 ml of 10% aqueous hydrochloric acid. The aqueous extract is decolorized with charcoal, filtered, and the filtrate is rendered alkaline with 10 ml of 10% aqueous sodium hydroxide solution. The resulting solution is extracted with 3×20 ml of ethyl ether. The etheral extracts are combined, dried over sodium sulfate, filtered, and the filtrate is evaporated to remove the solvent. The residue is dissolved in 40 ml of a 1:1 mixture of ethanol and acetone, the solution is cooled to 0° C., and dry gaseous hydrogen chloride is bubbled through the solution until the separation of crystals ceases. The separated salt is filtered off and recrystallized from 20 ml of ethanol. 5.1 g (56%) of the named compound are obtained; m.p.: 167°–168° C.

Similarly the following compounds are prepared from the appropriate starting substances:

3-[4-(2,5-dimethylphenyl)-piperazin-1-yl]-1-(furan-2-carbonyloxy)-propane dihydrochloride, m.p.: 210°–211° C.;

3-[4-(3-chlorophenyl)-piperazin-1-yl]-1-(furan-2-carbonyloxy)-propane dihydrochloride, m.p.: 170°–171° C.;

3-[4-(3,4-dichlorophenyl)-piperazin-1-yl]-1-(xanthene-9-carbonyloxy)-propane dihydrochloride, m.p.: 179°–180° C.;

3-[4-phenyl-piperazin-1-yl]-1-(furan-2-carbonyloxy)-propane dihydrochloride, m.p.: 166°–167° C.

We claim:

1. 3-[4-(3-methoxy-phenyl)-piperazin-1-yl]-1-(furan-2-carbonyloxy)-propane or a pharmaceutically effective acid addition or quaternary salt thereof.

* * * * *